(12) United States Patent
Thalgott et al.

(10) Patent No.: US 9,078,701 B2
(45) Date of Patent: Jul. 14, 2015

(54) SYSTEM AND METHOD FOR STABILIZING A POSTERIOR FUSION OVER MOTION SEGMENTS

(75) Inventors: John S. Thalgott, Las Vegas, NV (US); David T. Stinson, Woodinville, WA (US); Anthony J. Fennell, Redditch (GB); Jason E. Garber, Las Vegas, NV (US)

(73) Assignee: CENTINEL SPINE, INC., New York, NY (US)

( * ) Notice: Subject to any disclaimer, the term of this patent is extended or adjusted under 35 U.S.C. 154(b) by 241 days.

(21) Appl. No.: 12/941,213

(22) Filed: Nov. 8, 2010

(65) Prior Publication Data

US 2011/0190825 A1 Aug. 4, 2011

Related U.S. Application Data

(60) Provisional application No. 61/259,605, filed on Nov. 9, 2009.

(51) Int. Cl.
| | | |
|---|---|---|
| *A61B 17/04* | (2006.01) | |
| *A61B 17/70* | (2006.01) | |
| *F16B 39/24* | (2006.01) | |
| *A61B 17/88* | (2006.01) | |

(52) U.S. Cl.
CPC .............. *A61B 17/70* (2013.01); *A61B 17/88* (2013.01); *F16B 39/24* (2013.01)

(58) Field of Classification Search
CPC .... A61B 17/8965; A61B 17/686; F16B 39/24
USPC ........ 606/310, 246–279, 303–308; 623/17.11
See application file for complete search history.

(56) References Cited

U.S. PATENT DOCUMENTS

| | | | | |
|---|---|---|---|---|
| 4,988,351 | A * | 1/1991 | Paulos et al. ................... | 606/232 |
| 5,368,593 | A * | 11/1994 | Stark ............................. | 606/308 |
| 5,931,869 | A * | 8/1999 | Boucher et al. ............... | 128/898 |
| 5,997,541 | A * | 12/1999 | Schenk .......................... | 606/303 |
| 6,059,818 | A * | 5/2000 | Johnson et al. ................ | 606/232 |
| 6,524,315 | B1 * | 2/2003 | Selvitelli et al. ................ | 606/70 |
| 6,730,093 | B2 * | 5/2004 | Saint Martin ................. | 606/303 |
| 7,409,070 | B2 * | 8/2008 | Pitulia .......................... | 381/326 |
| 7,563,275 | B2 * | 7/2009 | Falahee et al. ................ | 606/328 |
| 7,635,379 | B2 * | 12/2009 | Callahan et al. ............... | 606/266 |
| 7,794,484 | B2 * | 9/2010 | Stone et al. .................... | 606/329 |
| 7,927,359 | B2 * | 4/2011 | Trautwein et al. ............ | 606/264 |
| 8,062,336 | B2 * | 11/2011 | Triplett et al. ................. | 606/247 |
| 8,083,775 | B2 * | 12/2011 | Winslow et al. ............... | 606/264 |
| 8,192,471 | B2 * | 6/2012 | Ludwig et al. ................ | 606/265 |
| 8,333,792 | B2 * | 12/2012 | Winslow et al. ............... | 606/305 |
| 8,486,120 | B2 * | 7/2013 | Shimko ......................... | 606/303 |
| 8,529,609 | B2 * | 9/2013 | Helgerson et al. ............ | 606/306 |
| 8,574,273 | B2 * | 11/2013 | Russell et al. ................. | 606/304 |
| 2002/0087161 | A1 * | 7/2002 | Randall et al. ................. | 606/73 |
| 2002/0133158 | A1 * | 9/2002 | Saint Martin .................. | 606/72 |
| 2002/0183747 | A1 * | 12/2002 | Jao et al. ........................ | 606/61 |

(Continued)

*Primary Examiner* — Eduardo C Robert
*Assistant Examiner* — Stuart S Bray
(74) *Attorney, Agent, or Firm* — MH2 Technology Law Group (57) ABSTRACT

A system and method for stabilizing adjacent vertebral bodies that have been fused is provided. The system and method involves transversely securing the bony segments of fused vertebral bodies together. In accordance with one exemplary embodiment, translaminar screws may be employed to transfix the facet joints of one or more motion segments. The motion segment may further include the presence of a spinal fusion implant or other internal fixation device.

5 Claims, 8 Drawing Sheets

(56) References Cited

U.S. PATENT DOCUMENTS

| | | | |
|---|---|---|---|
| 2003/0077143 A1* | 4/2003 | Smolarek | 411/161 |
| 2003/0105465 A1* | 6/2003 | Schmieding et al. | 606/73 |
| 2003/0139811 A1* | 7/2003 | Watson et al. | 623/11.11 |
| 2003/0144666 A1* | 7/2003 | Bagga et al. | 606/61 |
| 2004/0260298 A1* | 12/2004 | Kaiser et al. | 606/72 |
| 2005/0033298 A1* | 2/2005 | Hawkes et al. | 606/61 |
| 2005/0149030 A1* | 7/2005 | Serhan et al. | 606/73 |
| 2005/0197700 A1* | 9/2005 | Boehm et al. | 623/17.11 |
| 2006/0052784 A1* | 3/2006 | Dant et al. | 606/61 |
| 2006/0074419 A1* | 4/2006 | Taylor et al. | 606/70 |
| 2006/0084989 A1* | 4/2006 | Dickinson et al. | 606/61 |
| 2006/0189991 A1* | 8/2006 | Bickley | 606/72 |
| 2006/0217713 A1* | 9/2006 | Serhan et al. | 606/61 |
| 2006/0217714 A1* | 9/2006 | Serhan et al. | 606/61 |
| 2006/0217715 A1* | 9/2006 | Serhan et al. | 606/61 |
| 2006/0235410 A1* | 10/2006 | Ralph et al. | 606/72 |
| 2007/0243040 A1* | 10/2007 | Chen | 411/161 |
| 2007/0260244 A1* | 11/2007 | Wolter | 606/60 |
| 2008/0161862 A1* | 7/2008 | Ensign | 606/303 |
| 2008/0234758 A1* | 9/2008 | Fisher et al. | 606/309 |
| 2008/0255622 A1* | 10/2008 | Mickiewicz et al. | 606/319 |
| 2008/0306555 A1* | 12/2008 | Patterson et al. | 606/303 |
| 2009/0149884 A1* | 6/2009 | Snyder et al. | 606/233 |
| 2009/0192551 A1* | 7/2009 | Cianfrani et al. | 606/301 |
| 2009/0275993 A1* | 11/2009 | Phan et al. | 606/315 |
| 2009/0287255 A1* | 11/2009 | Erickson et al. | 606/279 |
| 2009/0312798 A1* | 12/2009 | Varela | 606/247 |
| 2009/0326580 A1* | 12/2009 | Anderson et al. | 606/246 |
| 2010/0069969 A1* | 3/2010 | Ampuero et al. | 606/301 |
| 2010/0094356 A1* | 4/2010 | Varela et al. | 606/304 |
| 2010/0100185 A1* | 4/2010 | Trieu et al. | 623/17.16 |
| 2010/0174320 A1* | 7/2010 | Truckai et al. | 606/279 |
| 2010/0185237 A1* | 7/2010 | Ratron | 606/232 |
| 2010/0241170 A1* | 9/2010 | Cammisa et al. | 606/264 |
| 2011/0015682 A1* | 1/2011 | Lewis et al. | 606/305 |
| 2011/0087296 A1* | 4/2011 | Reiley et al. | 606/303 |
| 2011/0106172 A1* | 5/2011 | Wallenstein et al. | 606/286 |
| 2011/0137352 A1* | 6/2011 | Biedermann et al. | 606/305 |
| 2011/0166656 A1 | 7/2011 | Thalgott et al. | |
| 2011/0166657 A1 | 7/2011 | Thalgott et al. | |
| 2011/0282396 A1* | 11/2011 | Shimko | 606/303 |
| 2011/0288598 A1* | 11/2011 | Moed et al. | 606/303 |
| 2011/0313466 A1* | 12/2011 | Butler et al. | 606/279 |
| 2011/0313472 A1* | 12/2011 | Yap et al. | 606/305 |
| 2012/0004690 A1* | 1/2012 | Gonzalez-Hernandez | 606/305 |
| 2012/0016372 A1* | 1/2012 | Fauth et al. | 606/104 |
| 2012/0116460 A1* | 5/2012 | Gorek | 606/279 |
| 2012/0203348 A1* | 8/2012 | Michelson | 623/17.16 |
| 2013/0289628 A1* | 10/2013 | Fritzinger | 606/290 |

* cited by examiner

SYSTEM AND METHOD FOR STABILIZING A POSTERIOR FUSION OVER MOTION SEGMENTS

CROSS-REFERENCE TO RELATED APPLICATIONS

This application claims priority to U.S. Provisional No. 61/259,605, filed Nov. 9, 2009, and entitled "SYSTEM AND METHOD FOR STABILIZING A POSTERIOR FUSION OVER MOTION SEGMENTS," which is herein incorporated by reference in its entirety.

FIELD

The present invention relates to orthopedic implants, and more particularly, to spinal implants that facilitate fusion of bone segments and associated methods. Even more particularly, the invention relates to a system and method for stabilizing vertebral motion segments.

BACKGROUND

The integrity of the spine, including its subcomponents like the vertebral bodies and intervertebral discs that are well known structural body parts forming the spine, are key to a patient's health. These parts may become crushed or damaged as a result of trauma or injury, or damaged by disease (e.g., by tumor, autoimmune disease) or as a result of wear over time or degeneration caused by the normal aging process.

In many instances, one or more structural body parts can be repaired or replaced with a prosthesis or implant. For example, specific to the spine, one method of repair is to remove the vertebra (in whole or in part) and/or the disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis may be configured to facilitate fusion between two adjacent vertebrae. The implant or prosthesis may be placed without attachment means or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a screw. Most implants and their attachment means are configured to provide an immediate, rigid fixation of the implant to the implantation site. In certain situations, it is desirable to provide additional stabilization after a posterior fusion over one or more motion segments.

Although the following discussion focuses on spinal implants or prostheses, it will be appreciated that many of the principles may equally be applied to other structural body parts within a human or animal body.

SUMMARY

The present disclosure provides a system and method for stabilizing adjacent vertebral bodies that have been fused by transversely securing the bony segments together. In accordance with one exemplary embodiment, a spinal stabilization system for transfixing a motion segment of a spine is provided. The system may include a pair of translaminar screws configured for insertion into facet joints of the motion segment, each screw comprising a shaft and a head region extending from the shaft. The system may also include a pair of captive washers configured for use with the translaminar screws, each washer comprising first and second complementary shaped plates for capturing the head region of the screw therebetween, the second plate further including a hole for receiving the shaft of the screw. The washers may include bone engaging features or surface treatments to promote bony ingrowth. In addition, the screws and washers permit a range of motion of about 25 to about 35 degrees.

In another exemplary embodiment of the present disclosure, a method is provided for transfixing a motion segment of a spine. The method involves providing a pair of translaminar screws configured for insertion into facet joints of the motion segment, each screw comprising a shaft and a head region extending from the shaft, and a pair of captive washers configured for use with the translaminar screws, each washer comprising first and second complementary shaped plates for capturing the head region of the screw therebetween, the second plate further including a hole for receiving the shaft of the screw. One of the pair of translaminar screws is inserted into a facet joint of the motion segment, while the other of the pair of translaminar screws is inserted into a facet joint on the opposite side of the motion segment. The motion segment further includes the presence of another stabilization implant.

Additional features of the disclosure will be set forth in part in the description which follows or may be learned by practice of the disclosure.

It is to be understood that both the foregoing general description and the following detailed description are exemplary and explanatory only and are not restrictive of the disclosure.

DESCRIPTION OF THE EMBODIMENTS

Figure 1:
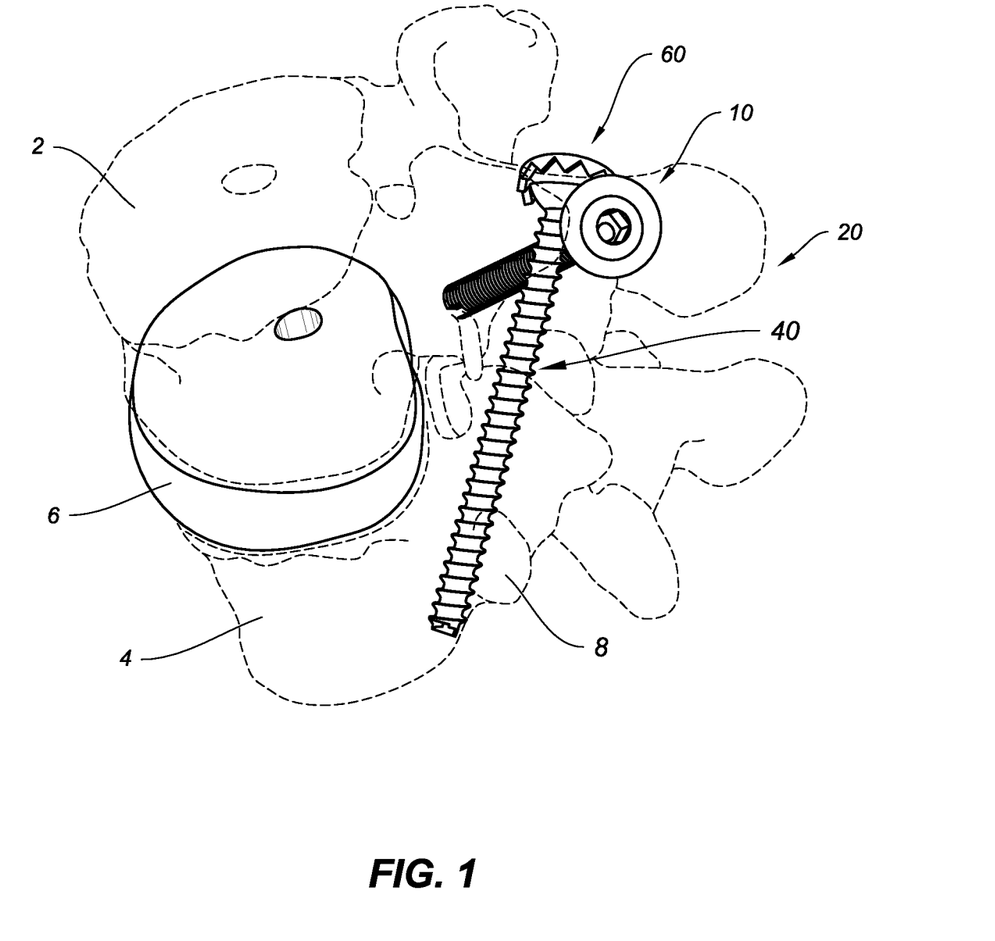
FIG. 1 illustrates a perspective cutaway view of an exemplary embodiment of a stabilization system of the present invention in situ.

The present disclosure provides a system and method for stabilizing adjacent vertebral bodies that have been fused by transversely securing the bony segments together. As shown in FIG. 1, a stabilization system 20 may be provided having translaminar screws 40 and washers 60. The stabilization system 20 may be employed to transfix the facet joints 8 of one or more motion segments, such as vertebral bodies 2, 4 and intervertebral disc 6, in short segments. In the embodiment shown in FIG. 1, the stabilization system 20 is not accompanied by a fusion implant. However, it is understood that the stabilization system 20 of the present invention can be used in concert with many types of known fusion enabling devices or implants in any region of the spine. Accordingly, FIG. 1 is intended to show the relative positioning of the stabilization system 20 isolated in situ, with the screws 40 shown exaggerated in scale for emphasis.

Figure 2A:
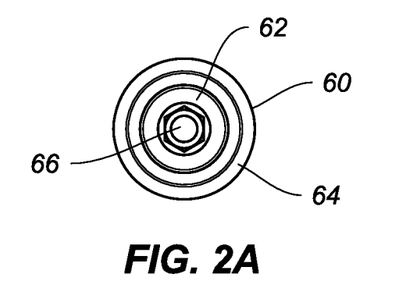
FIG. 2A illustrates a top view of a washer component of the stabilization system of FIG. 1.
Figure 2B:
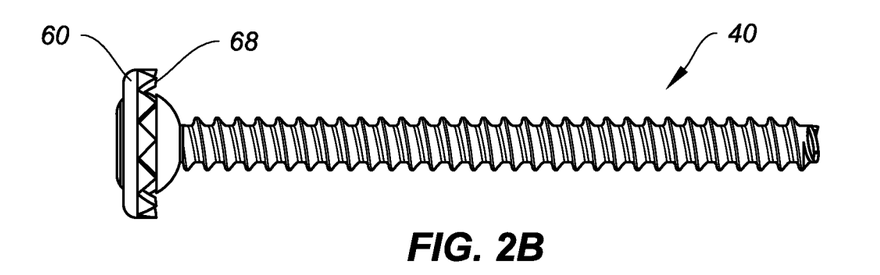
FIG. 2B illustrates a perspective side view of an exemplary embodiment of a screw component of the stabilization system of FIG. 1.
Figure 2C:
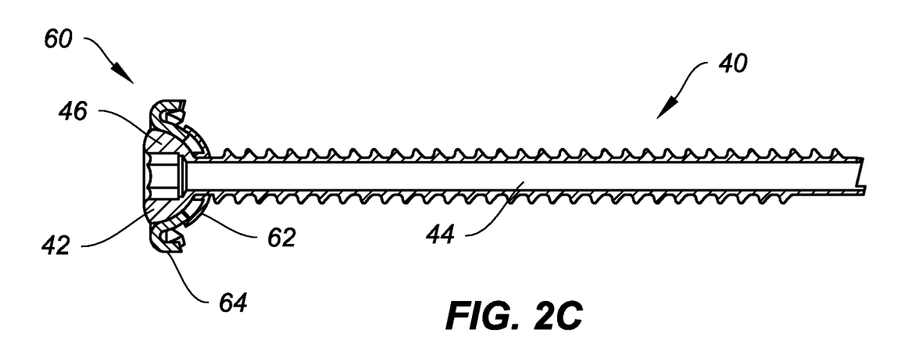
FIG. 2C illustrates a cross-sectional view of the screw component of FIG. 2B.

FIGS. 2A-2C show in greater detail the washer 60 and screw 40 of stabilization system 20. Referring now to FIG. 2A, the washer 60 comprises a lower plate 62 and an upper plate 64. Lower plate may have a lumen 66 to accommodate the shaft 44 of screw 40. Referring now to FIG. 2B, the washer 60 may also include teeth 68 or another equivalent bone engaging feature such as barbs. As shown in FIG. 2C, the shaft 44 extends from a head region 42 having an underside 46 that is contoured to seat within upper plate 64. The upper and lower plates 62, 64 of washer 60 form a captive washer for head region 42. The complementary shape of the underside 46 and the upper plate 64 allows for a predetermined range of motion relative to one another. In one embodiment, the geometry of the complementary shape supports a range of motion in the range of about 25 to about 35 degrees.

Figure 3A:
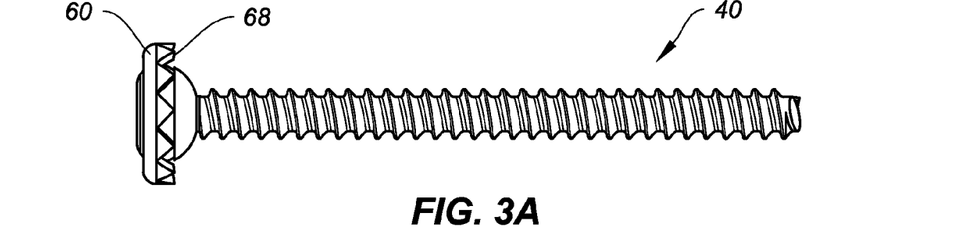
FIG. 3A illustrates a side view of another exemplary embodiment of a screw component of the stabilization system of FIG. 1.
Figure 3B:
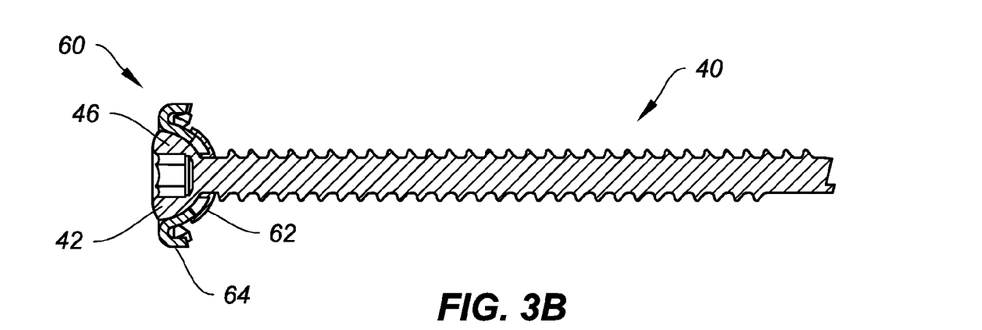
FIG. 3B illustrates a cross-sectional view of the screw component of FIG. 3A.

As further shown, the shaft 44 may be cannulated to accommodate wire-guided insertion. However, it is contemplated that the screw may be a solid body (i.e., solid core) screw as well, as shown in FIGS. 3A and 3B. Both cannulated and uncannulated versions of the translaminar screws 40 may be used interchangeably. Referring now to FIGS. 3A and 3B, an uncannulated screw 40 similar to the one described above is shown, with the same features and configured to be used with the same washer 60, but having no through-hole for wire insertion. In both instances with the cannulated and uncannulated versions of the screws 40, the major and minor diameters of the screw thread may be selected to balance the limited space for installing two or more screws transversely, while providing sufficient shear strength. In general, it is preferable to have the smallest possible major/minor diameters for the screws 40 to allow for ease of insertion, especially to accommodate insertion of the second screw.

In the illustrations, screw 40 is shown with a continuous thread along the length of the shaft 44 in its entirety. In other embodiments, the screw 40 is threaded only along a portion of the length of shaft 44, such as the portion that interfaces with the facet joint 8. The screw 40 may be a self-drilling and/or self-tapping. A large pitch for screw 40 may be helpful for certain embodiments. In addition, screw 40 should be configured to avoid any lag effect. In one embodiment, the threads may be of a buttress type.

The lower plate 62 of washer 60 may be surface treated to promote bony ingrowth. For example, the lower plate 62 may be sintered, plasma treated, or hydroxyapatite (HA) sprayed on all surfaces that interface with bone tissue.

In some embodiments, the present system 20 and associated method may be appropriate for patients having dislocations or subluxations from T12-L1 to the lumbosacral junction (L5-S1), supplementary internal fixation of degenerative spinal segments treated by an interbody fusion, or posterior alar-transverse or intertransverse fusion in degenerative disease of the spine.

Figure 4A:
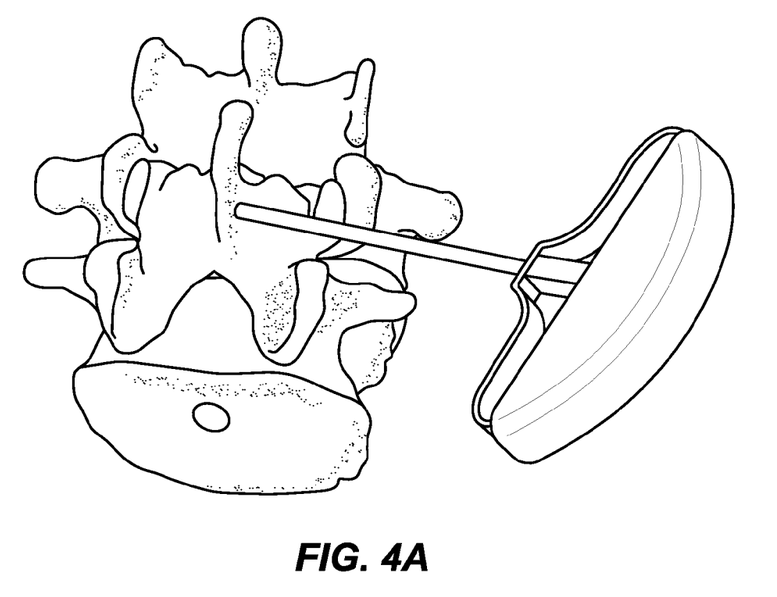
FIGS. 4A-4F represent steps in an exemplary method of installing the stabilization system of FIG. 1.
Figure 4B:
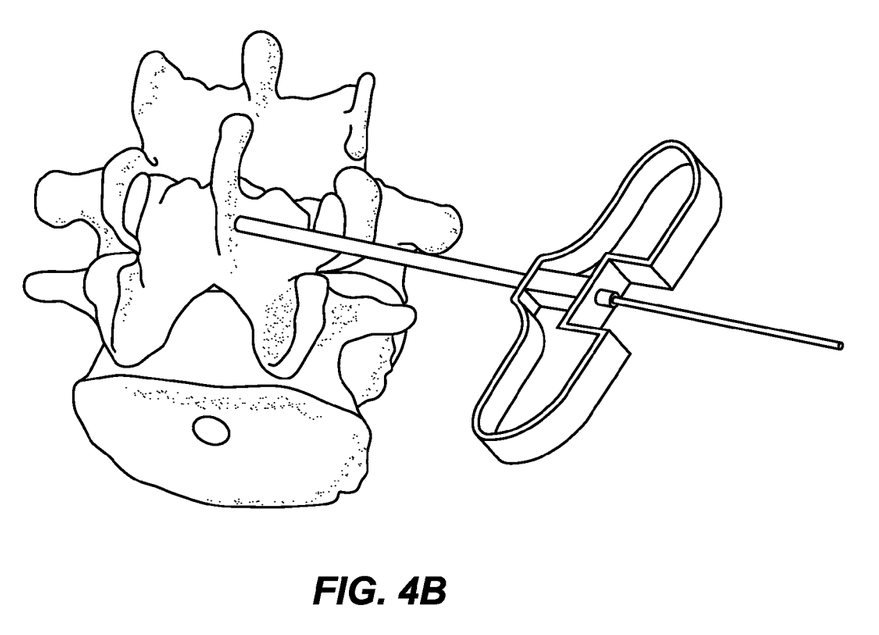

In an exemplary method of inserting the stabilization system 20, a Jamshidi needle may be percutaneously placed at the base of the spinous process 10 and inserted interlaminarly into the facet joint 8, as shown in FIG. 4A. Placement of the distal end of the Jamshidi needle may be provided with a unique geometry to fix a starting point and set the trajectory of the needle. Through the cannula of the Jamshidi needle, a guide pin can be advanced through to the facet joint 8, as shown in FIG. 4B.

Figure 4C:
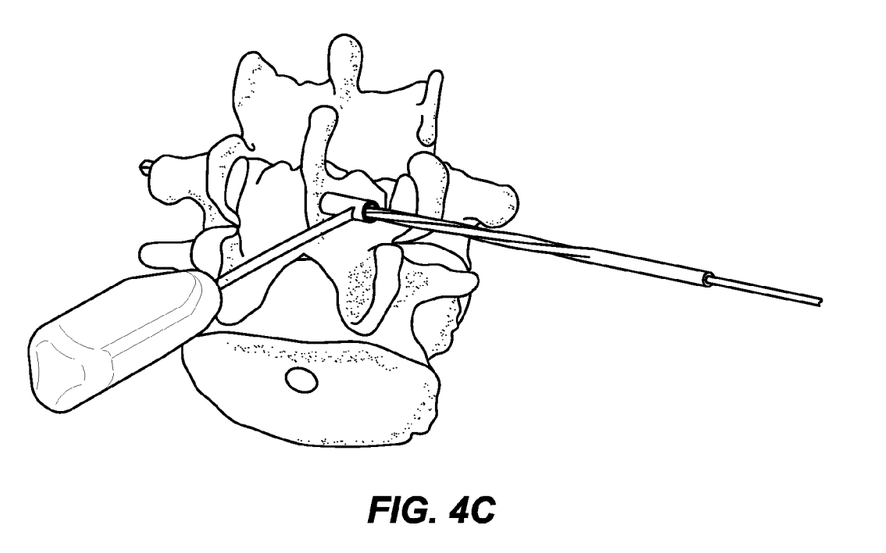
Figure 4D:
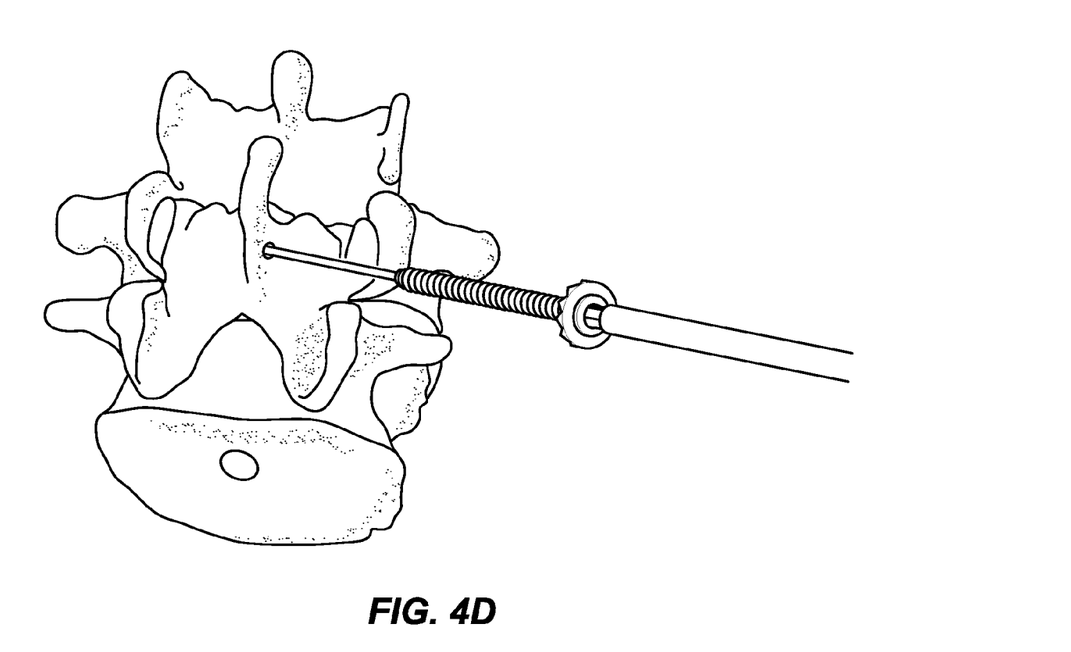
Figure 4E:
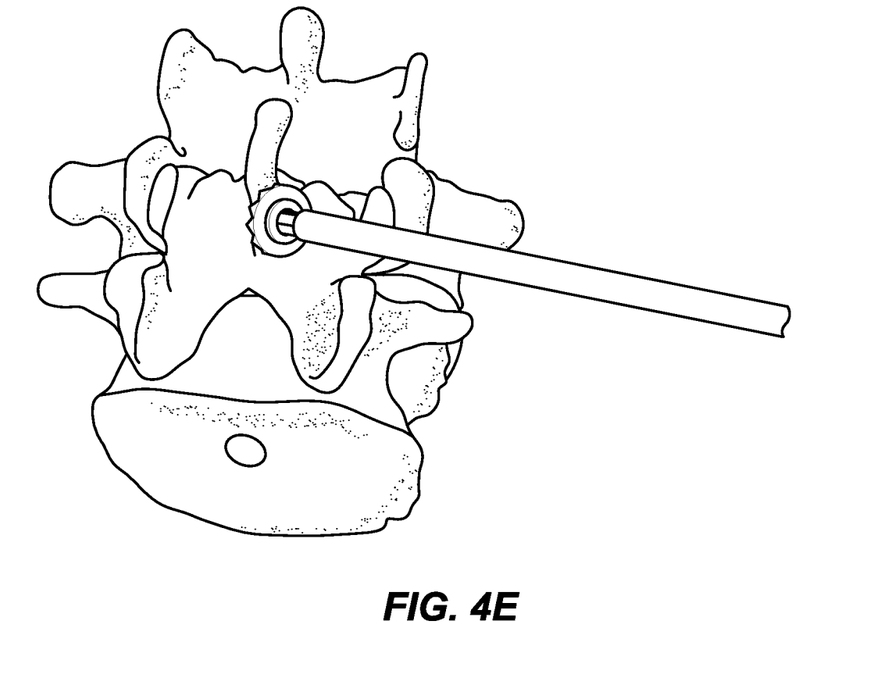
Figure 4F:
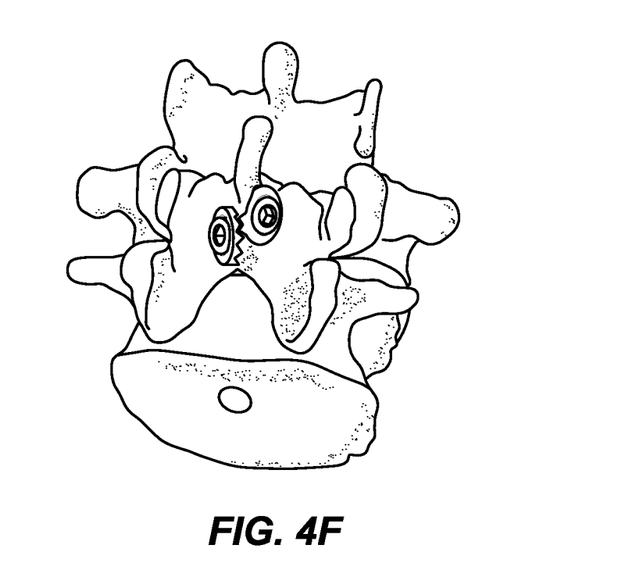

Next, as shown in FIG. 4C, a drill guide instrument can be percutaneously placed at the base of the spinous process 10 and advanced intralaminarly into the facet joint 8. The drill guide instrument may be configured with a distal end that is toothed to fix the starting point at the spinous process 10 and to provide a countersink that matches captive washer 60, in order to pre-set mating to the spinous process 10. For example, the handle of the instrument may be rotatable to create a profile on the cortical bone of the spinous process 10 to help seat the washer 60. After removing the guide instrument, the cannulated screw 40 may be placed over the guide wire and secured in place, as shown in FIGS. 4D and 4E. The surgeon may then repeat the steps above on the opposing side to transversely secure the screws 40 of the system 20 of the present invention as shown in FIG. 4F. Although two screws are shown, one skilled in the art will understand that any number of screws may be employed, such as one or three screws. Additionally, more than one stabilization system 20 may be used in a patient. For example, the process above may be repeated for a motion segment at a different level of the spine.

Figure 5:
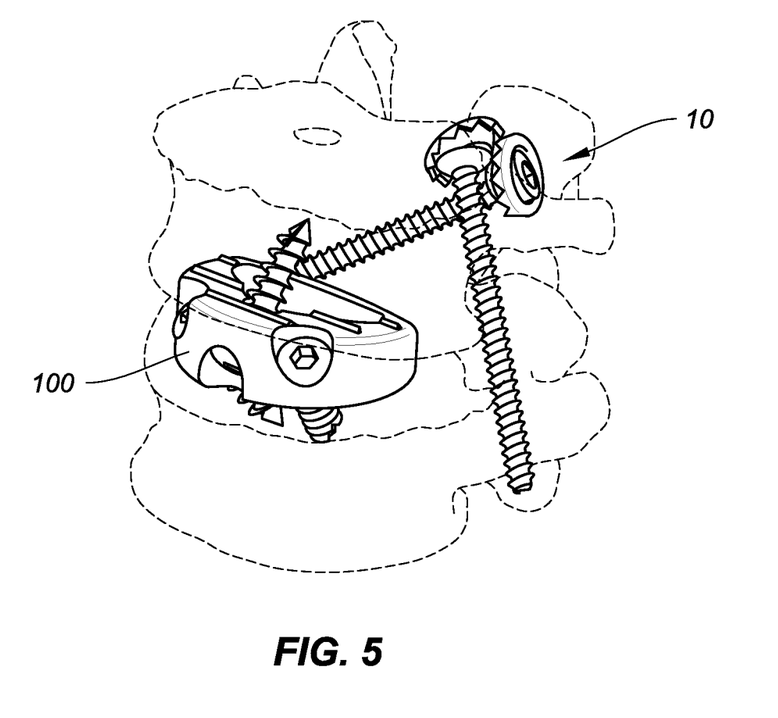
FIG. 5 illustrates a perspective cutaway view of the stabilization system of FIG. 1 used in concert with an exemplary spinal fusion implant.
Figure 6:
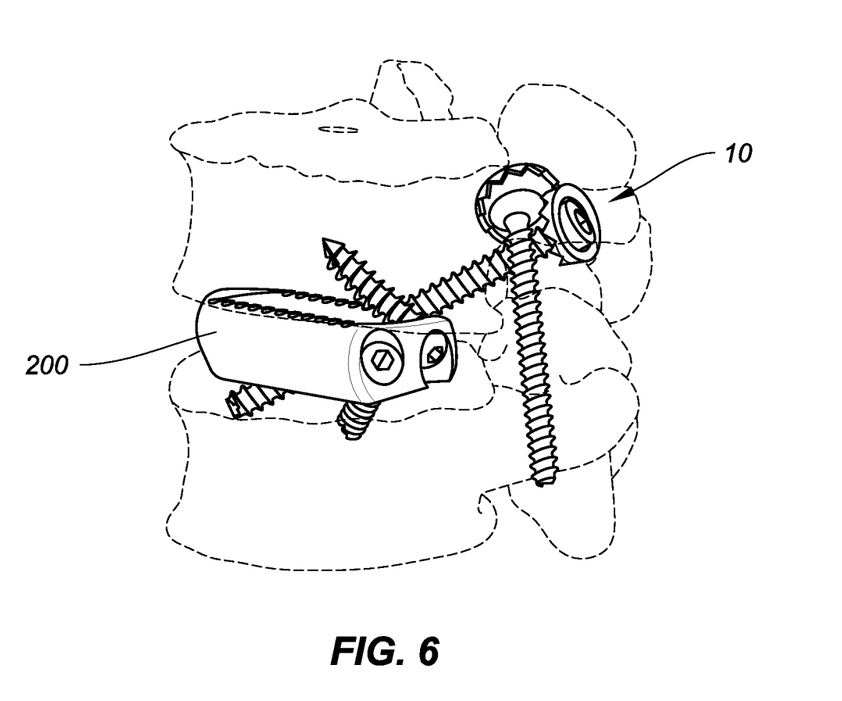
FIG. 6 illustrates a perspective cutaway view of the stabilization system of FIG. 1 used in concert with another exemplary spinal fusion implant.

FIGS. 5 and 6 represent other applications of the stabilization system 20 of the present invention in concert with exemplary stabilization implants, or fusion devices 100, 200, to supplement internal fixation. FIG. 5 illustrates an example of the stabilization system 20 used along with a spinal fusion device 100 similar to the one described in U.S. patent application Ser. No. 12/941,190, filed Nov. 8, 2010 and entitled "SPINAL IMPLANT CONFIGURED FOR MIDLINE INSERTION," while FIG. 6 illustrates an example of the stabilization system 20 used along with a spinal fusion device 200 similar to the one described in U.S. patent application Ser. No. 12/941,193, filed Nov. 8, 2010 and entitled "SPINAL IMPLANT CONFIGURED FOR LATERAL INSERTION," both of which are herein incorporated in their entirety by reference. Of course, it is contemplated that the stabilization system 20 may be used with any number of other types of stabilization implants or other internal fixation systems or devices.

It is to be understood that both the foregoing general description and the following detailed description are exemplary and explanatory only and are not restrictive of the disclosure. Other embodiments of the invention will be apparent to those skilled in the art from consideration of the specification and practice of the disclosure provided herein.

What is claimed is:

1. A method for transfixing a motion segment of a spine comprising:
providing a pair of translaminar screws configured for insertion into facet joints of the motion segment, each screw comprising a shaft and a head region extending from the shaft, the head region having a smooth, arcuate underside, and a pair of captive washers configured for use with the translaminar screws, each washer comprising a first, upper plate and a second, complementary shaped lower plate configured to allow sliding movement of the upper and lower plates relative to one another, each of the plates further including a central opening for receiving the shaft of the screw to capture the head region of the screw therein, wherein the central opening of the first, upper plate is larger than the central opening of the second, lower plate, the first and second plates each having a spherical contour that complements the smooth, arcuate underside of the head region such that the head region of the screw can be seated against, and slidingly move with respect to, the plates;

inserting one of the pair of translaminar screws into a facet joint of the motion segment; and inserting the other of the pair of translaminar screws into a facet joint on the opposite side of the motion segment;

wherein the motion segment further includes the presence of another stabilization implant.

2. The method of claim 1, wherein the stabilization implant is a spinal fusion implant.

3. The method of claim 1, further being repeated for a motion segment at a different level of the spine.

4. The method of claim 1, further including creating a countersink prior to inserting to accommodate each washer.

5. The method of claim 1, wherein the screws are inserted so as to cross over one another in situ.

* * * * *